(12) United States Patent
Hatzfeld et al.

(10) Patent No.: US 7,459,603 B2
(45) Date of Patent: Dec. 2, 2008

(54) PLANTS HAVING MODIFIED GROWTH CHARACTERISTICS AND METHOD FOR MAKING THE SAME

(75) Inventors: Yves Hatzfeld, Lille (FR); Valerie Frankard, Rhodes-Saint-Genèse (BE)

(73) Assignee: Cropdesign N.V., Zwijnaarde (BE)

( * ) Notice: Subject to any disclaimer, the term of this patent is extended or adjusted under 35 U.S.C. 154(b) by 154 days.

(21) Appl. No.: 10/551,228

(22) PCT Filed: Feb. 16, 2004

(86) PCT No.: PCT/EP2004/050136

§ 371 (c)(1),
(2), (4) Date: Sep. 28, 2005

(87) PCT Pub. No.: WO2004/087927

PCT Pub. Date: Oct. 14, 2004

(65) Prior Publication Data

US 2006/0253932 A1 Nov. 9, 2006

(30) Foreign Application Priority Data

Apr. 1, 2003 (EP) .................. 03075975

(51) Int. Cl.
*C12N 5/14* (2006.01)
*C12N 15/12* (2006.01)
(52) U.S. Cl. ..................... 800/278; 800/290
(58) Field of Classification Search ........... None
See application file for complete search history.

(56) References Cited

U.S. PATENT DOCUMENTS

2004/0168214 A1* 8/2004 Kwart et al. ............. 800/284

FOREIGN PATENT DOCUMENTS

WO 02/081707 A 10/2002

WO 03/085115 A 10/2003

OTHER PUBLICATIONS

GenBank Accession No. NP_565435, Jan. 2002.*
Lorenzo et al. Jan. 2002, Plant Cell Physiol. 43:27-34.*
Kano-Murakami et al 1993, FEBS 334:365-368.*
International Search Report of PCT/EP2004/050136, mailed Sep. 9, 2004.
Queitsch et al., "Heat Shock Protein 101 Plays a Crucial Role in Thermotolerance in Arabidopsis", Plant Cell, American Society of Plant Physiologists, vol. 12, Apr. 2000, pp. 479-492, XP002949024.
Young et al., "A transgene encoding a plasma membrane H=- ATPase that confers acid resistance in Arabidopsis thaliana seedlings", Genetics, vol. 149, No. 2, Jun. 1998, pp. 501-507, XP002292701.
Katiyar-Agarwal et al., "Heat tolerant basmati rice engineered by over-expression of hsp101.", Plant Molecular Biology, vol. 51, No. 5, Mar. 2003, pp. 677-686, XP002292846.
J. Dunwell, "Transgenic approaches to crop improvement", Journal of Experimental Botany, vol. 51, No. Spec. Issue, Feb. 2000, pp. 487-496, XP002292960.
Zhao et al. "Cosuppression of a plasma membraneH+-ATPase isoform impairs sucrose translocation, stomatal opening, plant growth, and male fertility", Plant Cell, vol. 12, No. 4, Apr. 2000, pp. 535-546, XP002292702.
Morsomme et al., "The plant plasma membrane H+-ATPase: Structure, function and regulation", Biochimica et Biophysica Acta, vol. 1465, No. 1-2, May 1, 2000, pp. 1-16, XP002292704.
Schumacher et al., "The Arabidopsis det3 mutant reveals a central role for the vacuolar H+-ATPase in plant growth and development", Genes and Development, vol. 13, No. 24, Dec. 15, 1999, pp. 3259-3270, XP002292703.

* cited by examiner

*Primary Examiner*—Stuart F. Baum
*Assistant Examiner*—Li Zheng
(74) *Attorney, Agent, or Firm*—Nixon & Vanderhye P.C.

(57) ABSTRACT

The present invention concerns a method for modifying the growth characteristics of plants by modulating expression in a plant of a nucleic acid sequence encoding a TAD protein and/or modulating activity in a plant of a TAD protein. The invention also relates to transgenic plants having modified growth characteristics, which plants have modulated expression of a nucleic acid encoding a TAD protein fragment.

5 Claims, 3 Drawing Sheets

SEQ ID NO 1: CDS0671 coding sequence from LIMS, start and stop codon in bold aattcccgggatatcgtcgacccacgcgtccgaataaatctgcttttggaaacattgtg
ttgcatccttctcttcagaggagaatagaacacctcgctagggccacagcaaacaccaa
gtctcaccaggcaccatttcgcaatatgctcttttatggtcctcctggcactgggaaa
acaatggttgctagggagatcgcaagaaaatcgggtttggactatgccatgatgactgg
aggggatgttgcaccctgggtgcacaggctgtcaccaaaattcacgagatattcgatt
gggccaaaaaatcaaataaaggcctactgcttttcattgatgaggctgatgcattttg
tgcgagcggaatagtacatacatgagtgaagctcagcgaagtgctttaaatgctttact
ctttcgaacaggggaccagtcccgagacgtagttcttgtccttgcgaccaacaggccag
gagatctagacagtgctgtcactgaccgtatagacgaagttatcgaattccctctccct
caagaagaagagcgtttcaaattgctgaagctctatttgaacaagtaccttgctggtga
aggagacagtgacagcaattctaagtgggggcacctcttcaagaagaaccaacaaaaga
ggataaccatacaagatttgtctgatgatgtgattagagaggctgctaagaagatagaa
ggattctctggccgtgagattgcaaaacttatggcaagtgttcaagcaactgtatatgg
gagcccagattgtgttcttgattctcaactgttcaaggaaatcgtagattacaaggtcg
ctgagcatcaccaacgaataaaactagctgctgaaggtatggagccaacttaccagggg
aattaactgacaccacaaagatacaagtgtctttcactgatacgaattgttgaaaatt
tgtttattatctctttggtagtattgcatgcaaaattcatttttccaaacttaggata
ttgtagtttaggtgtactatttctgcttggggaatgagcactggatggtggacgtgttt
cagggttcaatgggacgttacaatttgatgggtacatagctcacttgggctgtaattgt
attgattctgtggatcgcaggaaaatacatccattgaatagataaatagtaggcaaaac
atgaagtctctttgaaataggtctctgttatcaaatatcaactaacctatcttttgatt
accgcggccgctctagagtatccctcgaggggcccaagcttacgcgt

SEQ ID NO 2: CDS0671 deduced protein sequence

MLFYGPPGTGKTMVAREIARKSGLDYAMMTGGDVAPLGAQAVTKIHEIFDWAKKSNKGL
LLFIDEADAFLCERNSTYMSEAQRSALNALLFRTGDQSRDVVLVLATNRPGDLDSAVTD
RIDEVIEFPLPQEEERFKLLKLYLNKYLAGEGDSDSNSKWGHLFKKNQQKRITIQDLSD
DVIREAAKKIEGFSGREIAKLMASVQATVYGSPDCVLDSQLFKEIVDYKVAEHHQRIKL
AAEGMEPTYQGN

FIGURE 3

SEQ ID NO 3: expression cassette cttctacatcggcttaggtgtagcaacacgactttattattattattattattatt
attattttacaaaaatataaaatagatcagtccctcaccacaagtagagcaagttggtg
agttattgtaaagttctacaaagctaatttaaaagttattgcattaacttatttcatat
tacaaacaagagtgtcaatggaacaatgaaaaccatatgacatactataattttgtttt
tattattgaaattatataattcaaagagaataaatccacatagccgtaaagttctacat
gtggtgcattaccaaaatatatatagcttacaaaacatgacaagcttagtttgaaaaat
tgcaatccttatcacattgacacataaagtgagtgatgagtcataatattatttttcttt
gctacccatcatgtatatatgatagccacaaagttactttgatgatgatatcaaagaac
atttttaggtgcacctaacagaatatccaaataatatgactcacttagatcataataga
gcatcaagtaaaactaacactctaaagcaaccgatgggaaagcatctataaatagacaa
gcacaatgaaaatcctcatcatccttcaccacaattcaaatattatagttgaagcatag
tagtaatttaaatcaactagggatatcacaagtttgtacaaaaaagcaggctggtaccg
gtccggaattcccgggatatcgtcgacccacgcgtccgaataaatctgcttttggaaac
attgtgttgcatccttctcttcagaggagaatagaacacctcgctagggccacagcaaa
caccaagtctcaccaggcaccatttcgcaatatgctcttttatggtcctcctggcactg
ggaaaacaatggttgctagggagatcgcaagaaaatcgggtttggactatgccatgatg
actggaggggatgttgcaccctgggtgcacaggctgtcaccaaaattcacgagatatt
cgattgggccaaaaaatcaaataaaggcctactgcttttcattgatgaggctgatgcat
ttttgtgcgagcggaatagtacatacatgagtgaagctcagcgaagtgctttaaatgct
ttactctttcgaacaggggaccagtcccgagacgtagttcttgtccttgcgaccaacag
gccaggagatctagacagtgctgtcactgaccgtatagacgaagttatcgaattccctc
tccctcaagaagaagagcgtttcaaattgctgaagctctatttgaacaagtaccttgct
ggtgaaggagacagtgacagcaattctaagtggggcacctcttcaagaagaaccaaca
aaagaggataaccatacaagatttgtctgatgatgtgattagagaggctgctaagaaga
tagaaggattctctggccgtgagattgcaaaacttatggcaagtgttcaagcaactgta
tatgggagcccagattgtgttcttgattctcaactgttcaaggaaatcgtagattacaa
ggtcgctgagcatcaccaacgaataaaactagctgctgaaggtatggagccaacttacc
aggggaattaactgacaccacaaagatacaagtgtctttcactgatacgaattgttgaa
aatttgtttattatctctttggtagtattgcatgcaaaattcattttttccaaacttag
gatattgtagtttaggtgtactatttctgcttggggaatgagcactggatggtggacgt
gtttcagggttcaatgggacgttacaatttgatgggtacatagctcacttgggctgtaa
ttgtattgattctgtggatcgcaggaaaatacatccattgaatagataaatagtaggca
aaacatgaagtctctttgaaataggtctctgttatcaaatatcaactaacctatcttt
gattaccgcggccgctctagagtatccctcgaggggcccaagcttacgcgtacccagct
ttcttgtacaaagtggtgatatcacaagcccggcggtcttctagggataacagggtaa
ttatatccctctagatcacaagcccggcggtcttctacgatgattgagtaataatgtg
tcacgcatcaccatgggtggcagtgtcagtgtgagcaatgacctgaatgaacaattgaa
atgaaaagaaaaaaagtactccatctgttccaaattaaaattcattttaaccttttaat
aggtttatacaataattgatatatgttttctgtatatgtctaatttgttatcatccggg
cggtcttctagggataacagggtaattatatccctctagacaacacacaacaaataaga
gaaaaacaaataatattaatttgagaatgaacaaaaggaccatatcattcattaactc
ttctccatccatttccatttcacagttcgatagcgaaaaccgaataaaaacacagtaa
attacaagcacaacaaatggtacaagaaaaacagttttcccaatgccataatactcgaa
c

FIGURE 3 (continued)

SEQUENCE LISTING

```
<160> NUMBER OF SEQ ID NOS: 3

<210> SEQ ID NO 1
<211> LENGTH: 1284
<212> TYPE: DNA
<213> ORGANISM: Nicotiana tabacum

<400> SEQUENCE: 1
aattcccggg atatcgtcga cccacgcgtc cgaataaatc tgcttttgga aacattgtgt      60
tgcatccttc tcttcagagg agaatagaac acctcgctag ggccacagca aacaccaagt     120
ctcaccaggc accatttcgc aatatgctct tttatggtcc tcctggcact gggaaaacaa     180
tggttgctag ggagatcgca agaaaatcgg gtttggacta tgccatgatg actggagggg     240
atgttgcacc cctgggtgca caggctgtca ccaaaattca cgagatattc gattgggcca     300
aaaaatcaaa taaaggccta ctgcttttca ttgatgaggc tgatgcattt ttgtgcgagc     360
ggaatagtac atacatgagt gaagctcagc gaagtgcttt aaatgcttta ctctttcgaa     420
caggggacca gtcccgagac gtagttcttg tccttgcgac caacaggcca ggagatctag     480
acagtgctgt cactgaccgt atagacgaag ttatcgaatt ccctctccct caagaagaag     540
agcgtttcaa attgctgaag ctctatttga acaagtacct tgctggtgaa ggagacagtg     600
acagcaattc taagtggggg cacctcttca agaagaacca acaaaagagg ataaccatac     660
aagatttgtc tgatgatgtg attagagagg ctgctaagaa gatagaagga ttctctggcc     720
gtgagattgc aaaacttatg gcaagtgttc aagcaactgt atatgggagc ccagattgtg     780
ttcttgattc tcaactgttc aaggaaatcg tagattacaa ggtcgctgag catcaccaac     840
gaataaaact agctgctgaa ggtatggagc caacttacca ggggaattaa ctgacaccac     900
aaagatacaa gtgtcttttca ctgatacgaa ttgttgaaaa tttgtttatt atctctttgg     960
tagtattgca tgcaaaattc attttttcca aacttaggat attgtagttt aggtgtacta    1020
tttctgcttg gggaatgagc actggatggt ggacgtgttt cagggttcaa tgggacgtta    1080
caatttgatg ggtacatagc tcacttgggc tgtaattgta ttgattctgt ggatcgcagg    1140
aaaatacatc cattgaatag ataaatagta ggcaaaacat gaagtctctt tgaaataggt    1200
ctctgttatc aaatatcaac taacctatct tttgattacc gcggccgctc tagagtatcc    1260
ctcgaggggc ccaagcttac gcgt                                           1284

<210> SEQ ID NO 2
<211> LENGTH: 248
<212> TYPE: PRT
<213> ORGANISM: Nicotiana tabacum

<400> SEQUENCE: 2

Met Leu Phe Tyr Gly Pro Pro Gly Thr Gly Lys Thr Met Val Ala Arg
1               5                   10                  15

Glu Ile Ala Arg Lys Ser Gly Leu Asp Tyr Ala Met Met Thr Gly Gly
                20                  25                  30
```

-continued

```
Asp Val Ala Pro Leu Gly Ala Gln Ala Val Thr Lys Ile His Glu Ile
             35                  40                  45
Phe Asp Trp Ala Lys Lys Ser Asn Lys Gly Leu Leu Leu Phe Ile Asp
     50                  55                  60
Glu Ala Asp Ala Phe Leu Cys Glu Arg Asn Ser Thr Tyr Met Ser Glu
 65                  70                  75                  80
Ala Gln Arg Ser Ala Leu Asn Ala Leu Leu Phe Arg Thr Gly Asp Gln
                 85                  90                  95
Ser Arg Asp Val Val Leu Val Leu Ala Thr Asn Arg Pro Gly Asp Leu
            100                 105                 110
Asp Ser Ala Val Thr Asp Arg Ile Asp Glu Val Ile Glu Phe Pro Leu
            115                 120                 125
Pro Gln Glu Glu Glu Arg Phe Lys Leu Leu Lys Leu Tyr Leu Asn Lys
            130                 135                 140
Tyr Leu Ala Gly Glu Gly Asp Ser Asp Ser Asn Ser Lys Trp Gly His
145                 150                 155                 160
Leu Phe Lys Lys Asn Gln Gln Lys Arg Ile Thr Ile Gln Asp Leu Ser
                165                 170                 175
Asp Asp Val Ile Arg Glu Ala Ala Lys Lys Ile Glu Gly Phe Ser Gly
            180                 185                 190
Arg Glu Ile Ala Lys Leu Met Ala Ser Val Gln Ala Thr Val Tyr Gly
            195                 200                 205
Ser Pro Asp Cys Val Leu Asp Ser Gln Leu Phe Lys Glu Ile Val Asp
    210                 215                 220
Tyr Lys Val Ala Glu His His Gln Arg Ile Lys Leu Ala Ala Glu Gly
225                 230                 235                 240
Met Glu Pro Thr Tyr Gln Gly Asn
                245

<210> SEQ ID NO 3
<211> LENGTH: 2538
<212> TYPE: DNA
<213> ORGANISM: Artificial sequence
<220> FEATURE:
<223> OTHER INFORMATION: Expression cassette

<400> SEQUENCE: 3
cttctacatc ggcttaggtg tagcaacacg actttattat tattattatt attattatta      60
ttatttaca aaaatataaa atagatcagt ccctcaccac aagtagagca agttggtgag     120
ttattgtaaa gttctacaaa gctaatttaa aagttattgc attaacttat ttcatattac     180
aaacaagagt gtcaatggaa caatgaaaac catatgacat actataattt tgtttttatt     240
attgaaatta tataattcaa agagaataaa tccacatagc cgtaaagttc tacatgtggt     300
gcattaccaa aatatatata gcttacaaaa catgacaagc ttagtttgaa aaattgcaat     360
ccttatcaca ttgacacata agtgagtga tgagtcataa tattattttc tttgctaccc     420
atcatgtata tatgatagcc acaaagttac tttgatgatg atatcaaaga acattttttag    480
gtgcacctaa cagaatatcc aaataatatg actcacttag atcataatag agcatcaagt     540
aaaactaaca ctctaaagca accgatggga agcatctat aaatagacaa gcacaatgaa      600
aatcctcatc atccttcacc acaattcaaa tattatagtt gaagcatagt agtaatttaa     660
atcaactagg gatatcacaa gtttgtacaa aaaagcaggc tggtaccggt ccggaattcc     720
cgggatatcg tcgacccacg cgtccgaata aatctgcttt tggaaacatt gtgttgcatc     780
```

```
cttctcttca gaggagaata gaacacctcg ctagggccac agcaaacacc aagtctcacc    840
aggcaccatt tcgcaatatg ctcttttatg gtcctcctgg cactgggaaa acaatggttg    900
ctagggagat cgcaagaaaa tcgggtttgg actatgccat gatgactgga ggggatgttg    960 caccccctggg tgcacaggct gtcaccaaaa ttcacgagat attcgattgg gccaaaaaat   1020
caaataaagg cctactgctt ttcattgatg aggctgatgc attttttgtgc gagcggaata   1080 gtacatacat gagtgaagct cagcgaagtg ctttaaatgc tttactcttt cgaacagggg    1140
accagtcccg agacgtagtt cttgtccttg cgaccaacag gccaggagat ctagacagtg    1200
ctgtcactga ccgtatagac gaagttatcg aattccctct ccctcaagaa gaagagcgtt    1260
tcaaattgct gaagctctat ttgaacaagt accttgctgg tgaaggagac agtgacagca    1320
attctaagtg ggggcacctc ttcaagaaga accaacaaaa gaggataacc atacaagatt    1380
tgtctgatga tgtgattaga gaggctgcta agaagataga aggattctct ggccgtgaga    1440
ttgcaaaact tatggcaagt gttcaagcaa ctgtatatgg gagcccagat tgtgttcttg    1500
attctcaact gttcaaggaa atcgtagatt acaaggtcgc tgagcatcac caacgaataa    1560
aactagctgc tgaaggtatg gagccaactt accaggggaa ttaactgaca ccacaaagat    1620
acaagtgtct ttcactgata cgaattgttg aaaatttgtt tattatctct ttggtagtat    1680
tgcatgcaaa attcattttt tccaaactta ggatattgta gtttaggtgt actatttctg    1740
cttggggaat gagcactgga tggtggacgt gtttcagggt tcaatgggac gttacaattt    1800
gatgggtaca tagctcactt gggctgtaat tgtattgatt ctgtggatcg caggaaaata    1860
catccattga atagataaat agtaggcaaa acatgaagtc tctttgaaat aggtctctgt    1920
tatcaaatat caactaacct atcttttgat taccgcggcc gctctagagt atccctcgag    1980
gggcccaagc ttacgcgtac ccagctttct tgtacaaagt ggtgatatca caagcccggg    2040
cggtcttcta gggataacag ggtaattata tccctctaga tcacaagccc gggcggtctt    2100
ctacgatgat tgagtaataa tgtgtcacgc atcaccatgg gtggcagtgt cagtgtgagc    2160
aatgacctga atgaacaatt gaaatgaaaa gaaaaaaagt actccatctg ttccaaatta    2220
aaattcattt taacctttta ataggtttat acaataattg atatatgttt tctgtatatg    2280
tctaatttgt tatcatccgg gcggtcttct agggataaca gggtaattat atccctctag    2340
acaacacaca acaaataaga gaaaaaacaa ataatattaa tttgagaatg aacaaaagga    2400
ccatatcatt cattaactct tctccatcca tttccatttc acagttcgat agcgaaaacc    2460
gaataaaaaa cacagtaaat tacaagcaca acaaatggta caagaaaaac agttttccca    2520
atgccataat actcgaac                                                  2538
```

PLANTS HAVING MODIFIED GROWTH CHARACTERISTICS AND METHOD FOR MAKING THE SAME

This application is the U.S. national phase of international application PCT/EP2004/050136, filed 16 Feb. 2004, which designated the U.S. and claims priority of EP 03075975.7, dated 1 Apr. 2003, the entire contents of each of which are hereby incorporated by reference.

FIELD OF THE INVENTION

The present invention concerns a method for modifying plant growth characteristics. More specifically, the present invention concerns a method for increasing yield by modulating expression of a nucleic acid sequence encoding a TAD protein and/or activity of a TAD protein in a plant. The present invention also concerns plants having modulated expression of a nucleic acid sequence encoding a TAD protein and/or modulated activity of a TAD protein, which plants have increase yield relative to corresponding wild type plants.

BACKGROUND OF THE INVENTION

The AAA protein family (ATPases Associated with various cellular Activities, Kunau et al., Biochimie 75, 209-224, 1993) represents a large group of proteins that all share a highly conserved ATP binding domain of about 230 amino acids, exhibiting ATPase activity (Neuwald et al., Genome Research 9, 27-43, 1999; Vale, J. Cell Biol. 150, F13-F19, 2000). AAA proteins are widespread and have been characterised in Archaea, Eubacteria and all eukaryotic kingdoms. The AAA domains are required for protein functioning and are organised in hexameric rings that undergo conformational changes upon hydrolysis of ATP. This change in conformation, which is dependent on ATP hydrolysis, puts tension on bound proteins, and this mechanical activity allows unfolding of associated proteins, protein-protein dissociation etc. As a result, the AAA proteins play a role in different cellular processes, including cell cycle, organelle synthesis, mitochondrial functioning, vesicle transport, protein turnover, regulation of the cytoskeleton and intracellular motility. Thus, AAA proteins may represent a broad class of mechanoenzymes that have evolved unique ways of using a fundamentally similar conformational change in many different biological settings, but the basis of interaction with their target proteins is still a matter of speculation (Vale, 2000). So far, most efforts of research are focused on resolving the molecular structure and function of AAA ATPases, and consequently nothing is known about their role on a macroscopic level, such as plant growth or yield.

Given the ever-increasing world population, it remains a major goal of agricultural research to improve the efficiency of agriculture and to increase the diversity of plants in horticulture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic complements that may not always result in the desirable trait being passed on from parent plants. Advances in molecular biology have allowed mankind to manipulate the germplasm of animals and plants. Genetic engineering of plants entails the isolation and manipulation of genetic material (typically in the form of DNA or RNA) and the subsequent introduction of that genetic material into a plant. Such technology has led to the development of plants having various improved economic, agronomic or horticultural traits. A trait of particular economic interest is high yield.

DETAILED DESCRIPTION

Surprisingly, the inventors have found that modulating expression in a plant of a nucleic acid sequence encoding the ATPase domain derived from a TOB3 like protein (hereafter named TOB3 ATPase Domain, TAD) resulted in increased yield when compared to corresponding wild type plants.

Therefore according to a first embodiment of the present invention there is provided a method for increasing yield of a plant compared to corresponding wild type plants, comprising modulating expression in a plant of an isolated nucleic acid sequence encoding a TAD protein, or a homologue, derivative or active fragment thereof and/or modulating activity of a TAD, a homologue, derivative or active fragment thereof.

The term TAD encoding nucleic acid/gene, as defined herein, refers to any nucleic acid encoding an ATPase domain derived from a TOB3 like protein, or the complement thereof. The nucleic acid may be derived (either directly or indirectly (if subsequently modified)) from any source provided that the nucleic acid, when expressed in a plant, leads to modulated expression of a TAD nucleic add/gene. The nucleic acid may be isolated from a microbial source, such as bacteria, archaea, yeast or fungi, or from a plant, algal or animal source. This nucleic add may be substantially modified from its native form in composition and/or genomic environment through deliberate human manipulation. The nucleic acid molecule is preferably a homologous nucleic acid molecule, i.e. a structurally and/or functionally related nucleic acid molecule, preferably obtained from a plant, whether from the same plant species or different. The nucleic acid molecule may be isolated from a dicotyledonous species, preferably from the family Solanaceae, further preferably from *Nicotiana tabacum*. More preferably, the nucleic acid is as represented by SEQ ID NO: 1 or a portion thereof or is a nucleic acid molecule capable of hybridising therewith, which hybridising molecules encode proteins having TAD (ATP binding and/or ATP hydrolysing) activity, i.e. similar biological activity to that of SEQ ID NO: 1; or the nucleic acid encodes an amino acid represented by SEQ ID NO: 2 or encodes a homologue, derivative or active fragment thereof. The term TAD encoding nucleic acid/gene also encompasses variants of the nucleic acid encoding a TAD due to the degeneracy of the genetic code; allelic variants of the nucleic acid encoding a TAD; different splice variants of the nucleic add encoding a TAD and variants that are interrupted by one or more intervening sequences.

The term TAD protein, as defined herein, refers to proteins comprising an ATPase domain derived from any TOB3 like protein. Preferably the TAD is from *Nicotiana tabacum*, more preferably the TAD protein is a protein as represented by SEQ ID NO: 2, or is a homologue, derivative or active fragment thereof, which homologues, derivatives or active fragments have similar biological activity to that of SEQ ID NO: 2. Methods for measuring binding of ATP or for measuring ATPase activity are well known in the art.

Advantageously, the method according to the present invention may also be practised using portions of a sequence represented by SEQ ID NO: 1 or by using sequences that hybridise (preferably under stringent conditions) to SEQ ID NO: 1, which hybridising sequences perform the same biological function as SEQ ID NO 1 (that is: encode proteins having TAD activity), or by using nucleic acids encoding homologues, derivatives or active fragments of a sequence according to SEQ ID NO 2.

Homologues of SEQ ID NO 2 may be found in various prokaryotic and eukaryotic organisms. The closest homologues however are generally found in the plant kingdom. Suitable homologues of SEQ ID NO: 2 include other TAD domains present in proteins such as represented in GenBank Accessions NP_565435, NP_195376, AAL87170, BAD08048, NP_186956, BAD07862, NP_197195 or PIR accessions A84563 or T51548.

Methods for the search and identification of TAD homologues would be well within the realm of persons skilled in the art. Such methods comprise comparison of the sequences represented by SEQ ID NO 1 or 2 in a computer readable format with sequences that are available in public databases such as MIPS (URL mips.gsf.de), GenBank (URL ncbi.nlm.nih.gov/Genbank/index) or EMBL Nucleotide Sequence Database (URL ebi.ac.uk/embl/index), using algorithms well known in the art for alignment or comparison of sequences, such as GAP (Needleman and Wunsch, J. Mol. Biol. 48, 443-453 (1970)), BESTFIT (using the local homology algorithm of Smith and Waterman (Advances in Applied Mathematics 2, 482-489 (1981))), BLAST (Altschul, S. F., Gish, W., Miller, W., Myers, E. W. & Lipman, D. J., J. Mol. Biol. 215, 403-410 (1990)), FASTA and TFASTA (W. R. Pearson and D. J. Lipman, Proc. Natl. Acad. Sci. USA 85, 2444-2448 (1988)). The software for performing BLAST analysis is publicly available at the National Centre for Biotechnology Information.

These above-mentioned analyses for sequence homology can be done with a full-length query sequence or with certain regions of such a sequence, for example with conserved domains. Also the identification of family members of the TAD (as defined below) or the determination of the percentage of sequence identity between the TAD and a homologue (as defined below) can be performed by using these conserved sequences. The identification of such domains in a protein sequence would also be well within the realm of the person skilled in the art and involve a computer readable format of the nucleic acids used in the present invention, the use of alignment software programs and the use of publicly available information on protein domains, conserved motifs and boxes. An integrated search can be done using the INTERPRO database (Mulder et al., (2003) Nucl. Acids Res. 31, 315-318, http://www.ebi.ac.uk/interpro/scan.html) which combines several databases on protein families, domains and functional sites, such as the PRODOM (Servant et al., (2002) Briefings in Bioinformatics 3, 246-251, http://prodes.toulouse.inra.fr/prodom/2002.1/html/home.php), PIR (Huang et al. (2003) Nucl. Acids Res. 31, 390-392, http://pir.georgetown.edu/) or Pfam (Bateman et al. (2002) Nucl. Acids Res. 30, 276-280, URL pfam.wustl.edu) databases. Sequence analysis programs designed for motif searching can be used for identification of conserved fragments, regions and domains as mentioned above. Suitable computer programs to this end include for example MEME (Bailey and Elkan (1994) Proceedings of the Second International Conference on Intelligent Systems for Molecular Biology, pp. 28-36, AAAI Press, Menlo Park, Calif., http://meme.sdsc.edu/meme/website/intro.html).

The term TAD includes proteins homologous to a protein as presented in SEQ ID NO 2. "Homologues" of a TAD protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

When using an alignment program such as GAP, with a gap penalty of 10, an extend penalty of 0.5 and the BLOSUM 62 matrix, the homologues useful in the methods according to the invention have at least 70% sequence identity with SEQ ID NO 2 in that part of their protein sequence that corresponds to SEQ ID NO 2. Typically, the homologues have at least 80% sequence identity or similarity to SEQ ID NO 2, preferably at least 85% sequence identity or similarity, further preferably at least 90% sequence identity or similarity to SEQ ID NO 2, most preferably at least 95%, 96%, 97%, 98% or 99% sequence identity or similarity to SEQ ID NO 2. The percentage of similarity can also be calculated using alignment programs such as GAP.

The homologues useful in the method according to the invention can alternatively be defined as having ATP binding activity and/or ATPase activity, and comprising a sequence of 22 consecutive amino acid residues, which sequence is at least 90% identical to a corresponding sequence in SEQ ID NO 2.

Homologous proteins can be grouped in "protein families". A protein family can be defined by functional and sequence similarity analysis, using programs such as, for example, Clustal W. A neighbour-joining tree of proteins homologous to SEQ ID NO 2, generated by the Clustal W program gives a good overview of their structural and ancestral relationships. Advantageously also these family members are useful in the methods of the present invention.

Two special forms of homology, orthologous and paralogous homology, are evolutionary concepts used to describe ancestral relationships of genes. The term "paralogous" relates to homologous genes that result from one or more gene duplications within the genome of a species. The term "orthologous" relates to homologous genes in different organisms due to ancestral relationship of these genes. The term "homologues" as used herein also encompasses paralogues and orthologues of the proteins useful in the methods according to the invention. Orthologous genes can be identified by querying one or more gene databases with a query gene of interest, using for example the BLAST program. The highest-ranking subject genes that result from the search are then again subjected to a BLAST analysis, and only those subject genes that match again with the query gene are retained as true orthologous genes. For example, to find a rice orthologue of an *Arabidopsis thaliana* gene, one may perform a BLASTN or TBLASTX analysis on a rice database (such as (but not limited to) the *Oryza sativa* Nipponbare database available at the NCBI (URL ncbi.nlm.nih.gov or the genomic sequences of rice (cultivars indica or japonica)). In a next step, the obtained rice sequences are used in a reverse BLAST analysis using an *Arabidopsis* database. The results may be further refined when the resulting sequences are analysed with ClustalW and visualised in a neighbour joining tree. The method can be used to identify orthologues from many different species.

"Substitutional variants" of a protein are those in which at least one residue in an amino acid sequence has been removed and a different residue inserted in its place. Amino acid substitutions are typically of single residues, but may be clustered depending upon functional constraints placed upon the polypeptide. Preferably, amino acid substitutions comprise conservative amino add substitutions. "Insertional variants" of a protein are those in which one or more amino acid residues are introduced into a predetermined site in a protein. Insertions can comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_8$-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope. "Deletion variants" of a protein are characterised by the removal of one or more amino acids from the protein, deletions will generally range from about 1 to 20 residues. Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The term "derivatives" refers to peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a TAD encompass peptides, oligopeptides, polypeptides, proteins and enzymes which may comprise naturally occurring altered, glycosylated, acylated or non-naturally occurring amino add residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence to facilitate its detection, and non-naturally occurring amino acid residues relative to the amino acid sequence of a naturally-occurring protein. "Active fragments" of a TAD protein encompass at least five contiguous amino add residues of a protein, which residues retain similar biological and/or functional activity to the naturally occurring protein.

Advantageously, the methods according to the present invention may also be practised using portions of a DNA or nucleic add molecule, which portions retain TAD activity, i.e. a similar biological function to that of SEQ ID NO: 2. Portions of a DNA molecule refer to a piece of DNA derived or prepared from an original (larger) DNA molecule, which DNA portion, when expressed in a plant, gives rise to plants having modified growth characteristics. The portion may comprise many genes, with or without additional control elements, or may contain just spacer sequences.

The present invention also encompasses nucleic add molecules capable of hybridising with a nucleic acid molecule encoding a TAD protein, which nucleic add molecules may also be useful in practising the methods according to the invention. The term "hybridisation" as defined herein is a process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A$^+$) mRNA. The hybridisation process can furthermore occur with one of the complementary nucleic adds immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and micro array hybridisation. In order to allow hybridisation to occur, the nucleic add molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition.

For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. High stringency conditions for hybridisation thus include high temperature and/or low salt concentration (salts include NaCl and Na$_3$-citrate) but can also be influenced by the inclusion of formamide in the hybridisation buffer and/or lowering the concentration of compounds such as SDS (sodium dodecyl sulphate) in the hybridisation buffer and/or exclusion of compounds such as dextran sulphate or polyethylene glycol (promoting molecular crowding) from the hybridisation buffer. Sufficiently low stringency hybridisation conditions are particularly preferred for the isolation of nucleic adds homologous to the DNA sequences of the invention defined supra. Elements contributing to homology include allelism, degeneration of the genetic code and differences in preferred codon usage.

"Stringent hybridisation conditions" and "stringent hybridisation wash conditions" in the context of nucleic acid hybridisation experiments such as Southern and Northern hybridisations are sequence dependent and are different under different environmental parameters. For example, longer sequences hybridise specifically at higher temperatures. The T$_m$ is the temperature under defined ionic strength and pH, at which 50% of the target sequence hybridises to a perfectly matched probe. Specificity is typically the function of post-hybridisation washes. Critical factors of such washes include the ionic strength and temperature of the final wash solution. Generally, stringent conditions are selected to be about 50° C. lower than the thermal melting point (T$_m$) for the specific sequence at a defined ionic strength and pH. The T$_m$ is the temperature under defined ionic strength and pH, at which 50% of the target sequence hybridises to a perfectly matched probe. The T$_m$ is dependent upon the solution conditions and the base composition of the probe, and may be calculated using the following equation:

$$T_m = 79.8°C + (18.5 \times \log[Na^+]) + (58.4°C \times \%[G+C]) - (820 \times (\#bp \text{ in duplex})^{-1}) - (0.5 \times \% \text{ formamide})$$

More preferred stringent conditions are when the temperature is 20° C. below $T_m$, and the most preferred stringent conditions are when the temperature is 10° C. below $T_m$. Non-specific binding may also be controlled using any one of a number of known techniques such as, for example, blocking the membrane with protein containing solutions, additions of heterologous RNA, DNA, and SDS to the hybridisation buffer, and treatment with Rnase. Wash conditions are typically performed at or below hybridisation stringency. Generally, suitable stringent conditions for nucleic acid hybridisation assays or gene amplification detection procedures are as set forth above. More or less stringent conditions may also be selected.

For the purposes of defining the level of stringency, reference can conveniently be made to Sambrook et al. (2001) Molecular Cloning: a laboratory manual, 3$^{rd}$ Edition Cold Spring Harbor Laboratory Press, CSH, New York or to Current Protocols in Molecular Biology, John Wiley & Sons, N.Y. (1989). An example of low stringency conditions is 4-6×SSC/0.1-0.5% w/v SDS at 37-45° C. for 2-3 hours. Depending on the source and concentration of the nucleic acid involved in the hybridisation, alternative conditions of stringency may be employed such as medium stringent conditions. Examples of medium stringent conditions include 1-4×SSC/0.25% w/v SDS at ≧45° C. for 2-3 hours. An example of high stringency conditions includes 0.1-1×SSC/0.1% w/v SDS at 60° C. for 1-3 hours. The skilled artisan is aware of various parameters which may be altered during hybridisation and washing and which will either maintain or change the stringency conditions. For example, another stringent hybridisation condition is hybridisation at 4×SSC at 65° C., followed by a washing in 0.1×SSC, at 65° C. for about one hour. Alternatively, an exemplary stringent hybridisation condition is in 50% formamide, 4×SSC at 42° C. Still another example of stringent conditions include hybridisation at 62° C. in 6×SSC, 0.05×BLOTTO and washing at 2×SSC, 0.1% w/v SDS at 62° C.

The methods according to the present invention may also be practised using an alternative splice variant of a nucleic acid molecule encoding a TAD protein. The term "alternative splice variant" as used herein encompasses variants of a nucleic add molecule in which selected introns and/or exons have been excised, replaced or added. Such variants will be ones in which the biological activity of the protein remains unaffected, which can be achieved by selectively retaining functional segments of the protein. Such splice variants may be found in nature or can be manmade. Methods for making such splice variants are well known in the art. Thus the invention also encompasses methods for modifying the growth characteristics of plants, in particular for increasing yield, comprising modulating expression in a plant of an alternative splice variant of a nucleic acid molecule encoding a TAD and/or by modulating activity and/or levels of a TAD encoded by the alternative splice variant. Preferably, the splice variant is a splice variant of the sequence represented by SEQ ID NO: 1.

Advantageously, the methods according to the present invention may also be practised using allelic variants of a nucleic acid molecule encoding a TAD, preferably an allelic variant of a sequence represented by SEQ ID NO: 1. Allelic variants exist in nature and encompassed within the methods of the present invention is the use of these natural alleles. Allelic variants are further defined as to comprise single nucleotide polymorphisms (SNPs) as well as small insertion/deletion polymorphisms (INDELs; the size of INDELs is usually less than 100 bp). SNPs and INDELs form the largest set of sequence variants in naturally occurring polymorphic strains of most organisms. They are helpful in mapping genes and discovery of genes and gene functions. They are furthermore helpful in identification of genetic loci, e.g. plant genes, involved in determining processes such as growth rate, plant size and plant yield, plant vigour, disease resistance, stress tolerance etc. Many techniques are nowadays available to identify SNPs and/or INDELs including (i) PCR followed by denaturing high performance liquid chromatography (DHPLC; e.g. Cho et al. (1999) Nature Genet. 23, 203-207); (ii) constant denaturant capillary electrophoresis (CDCE) combined with high-fidelity PCR (e.g. Li-Sucholeiki et al., (1999) Electrophoresis 20, 1224-1232); (iii) denaturing gradient gel electrophoresis (Fischer and Lerman (1983) Proc. Natl. Acad. Sci. USA 80, 1579-1583); (iv) matrix-assisted laser desorption/ionization time-of-flight mass spectrometry (MALDI-TOF MS; e.g. Ross et al. (2000) Biotechniques 29, 620-629); (v) real-time fluorescence monitoring PCR assays (Tapp et al. (2000) Biotechniques 28, 732-738); (vi) Acrydite™ gel technology (Kenney et al. (1998) Biotechniques 25, 516-521); (vii) cycle dideoxy fingerprinting (CddF; Langemeier et al. (1994) Biotechniques 17, 484-490); (viii) single-strand conformation polymorphism (SSCP) analysis (Vidal-Puig and Moller (1994) Biotechniques 17, 490-496) and (ix) minisequencing primer extension reaction (Syvanen (1999) Hum. Mutat 13, 1-10). The technique of 'Targeting Induced Local Lesions in Genomes' (TILLING; McCallum et al. (2000) Nat. Biotechnol. 18, 455-457; Plant Physiol. 123, 439-442), which is a variant of (i) supra, can also be applied to rapidly identify an altered gene in e.g. chemically mutagenized plant individuals showing interesting phenotypes.

The use of these allelic variants in particular conventional breeding programmes, such as in marker-assisted breeding is also encompassed by the present invention; this may be in addition to their use in the methods according to the present invention. Such breeding programmes sometimes require the introduction of allelic variations in the plants by mutagenic treatment of a plant. One suitable mutagenic method is EMS mutagenesis. Identification of allelic variants then may take place by, for example, PCR. This is followed by a selection step for selection of superior allelic variants of the [name protein] sequence in question and which give rise to altered growth characteristics in a plant. Selection is typically carried out by monitoring growth performance of plants containing different allelic variants of the sequence in question, for example, different allelic variants of SEQ ID NO: 1. Monitoring growth performance can be done in a greenhouse or in the field. Further optional steps include crossing plants, in which the superior allelic variant was identified, with another plant. This could be used, for example, to make a combination of interesting phenotypic features. Therefore, as mutations in the TAD gene may occur naturally, they may form the basis for selection of plants showing higher yield.

The methods according to the present invention may also be practised by introducing into a plant at least a part of a (natural or artificial) chromosome (such as a Bacterial Artificial Chromosome (BAC)), which chromosome contains at least a gene/nucleic add molecule encoding a TAD (such as SEQ ID NO: 1), preferably together with one or more related genes from the same species or from the same family of genes, and/or nucleic add molecule(s) encoding regulatory proteins for TAD expression and/or activity. The present invention thus also encompasses a method for modifying growth characteristics of plants, in particular for increasing yield, by introducing into a plant a part of a chromosome comprising at least a gene/nucleic acid encoding a TAD, which gene/nucleic add encoding a TAD is under control of a seed-preferred promoter and which artificial chromosome preferably also comprises one or more related genes from the same species, and/or nucleic add sequence(s) encoding regulatory proteins for TAD expression and/or activity.

According to a preferred aspect of the present invention, overexpression (or increase of expression) of a nucleic acid is envisaged compared to corresponding wild type plants. Increasing or decreasing expression (or modulating expression) of a nucleic add encoding a TAD protein encompasses altered expression of this gene in the whole organism or in specific cells or tissues. Altered expression of a gene may be effected, for example by chemical means and/or recombinant means. Modulating expression of a TAD gene may be effected directly (i.e. through the modulation of expression of the concerned TAD encoding gene itself). In the direct approach, the modulated expression may result from altered expression levels of an endogenous TAD gene and/or may result from altered expression of a TAD encoding nucleic add that was previously introduced into a plant. Additionally or alternatively, the modulation of expression as mentioned above is effected in an indirect way, for example as a result of decreased or increased levels and/or activity of factors that control the expression of a TAD gene. The altered expression is to be understood as altered when compared to expression of a corresponding TAD protein in corresponding wild type plants.

Advantageously, modulation of expression of a nucleic acid encoding a TAD protein and/or modulation of activity and/or levels of the TAD protein itself may be effected by chemical means, i.e. by exogenous application of one or more compounds or elements capable of modulating expression of a TAD gene (which may be either an endogenous gene or a transgene introduced into a plant). The term "exogenous application" taken in its broadest context includes contacting or administering cells, tissues, organs or organisms with a suitable compound or element. The compound may be applied to a plant in a suitable form for uptake (such as through application to the soil for uptake via the roots, or by applying directly to the leaves, for example by spraying). Suitable compounds or elements for exogenous application include TAD encoding nucleic adds and nucleic acids that hybridise therewith. Additionally or alternatively, contacting or administering cells, tissues, organs or organisms with an interacting protein or with an inhibitor or activator of the gene provides another exogenous means for modulation of expression of a nucleic add encoding a TAD. Modulation of expression of a nucleic acid encoding a TAD protein may also be effected as a result of altered levels of factors that directly or indirectly activate or inactivate a TAD protein.

Furthermore, plants, seeds or other plant material can be subjected to treatment with mutagenic substances. Chemical substances effecting mutagenesis comprise N-nitroso-N-ethylurea, ethylene imine, ethyl methanesulphonate or diethyl sulphate. As an alternative, ionising radiation such as y-rays or X-rays can equally well be used. Methods for introducing mutations and testing the effect of mutations (such as modified protein expression and/or modified protein activity) are known in the art. Encompassed by mutagenesis are methods employing chemical mutagens, as well as physical mutagens, such as radiation. Any characteristic of the TAD protein can be altered by mutagenesis. For example these mutations can be responsible for the altered control of a TAD encoding gene, resulting in the desired expression level or expression pattern of the gene. In particular, these mutations can result in overexpression of TAD that is confined mainly to the seed. Alternatively and/or additionally, the activity or substrate specificity of the protein can be modified, or the affinity for a cofactor can be adapted. According to a preferred aspect of the invention said mutagenesis results in an increase in expression and/or activity and/or levels of a TAD protein in the plant seed.

Additionally or alternatively, and according to a preferred embodiment of the present invention, modulation of expression of a nucleic acid encoding a TAD and/or modulation of activity and/or levels of the TAD protein itself may be effected by recombinant means. Such recombinant means may comprise a direct and/or indirect approach for modulation of expression of a nucleic acid.

For example, an indirect recombinant approach may comprise introduction into a plant of a nucleic acid capable of modulating activity and/or levels of the protein in question (a TAD protein) and/or capable of modulating expression of the gene in question (a gene encoding a TAD protein). Examples of such nucleic acids to be introduced into a plant are nucleic adds encoding transcription factors, activators, inhibitors or other ligands that bind to the promoter of the TAD gene or that interact with the TAD protein. Methods to test these kinds of interaction and to isolate the nucleic acids encoding these interactors are for example yeast one-hybrid or yeast two-hybrid screening. The TAD gene or the TAD protein may be wild type, i.e. the native or endogenous nucleic acid or polypeptide. Alternatively, it may be a nucleic acid derived from the same or another species, which gene is introduced as a transgene, for example by transformation. This transgene may be substantially modified from its native form in composition and/or genomic environment through deliberate human manipulation. Also encompassed by an indirect approach for modulating expression of a TAD gene is the inhibition or simulation of regulatory sequences, or the provision of new regulatory sequences, that drive expression of the native gene encoding a TAD or the transgene encoding a TAD.

Such regulatory sequences may be introduced into a plant. For example, the regulatory sequence introduced into the plant is a promoter, capable of driving the expression of an endogenous TAD gene.

A direct and preferred approach for modulating expression of a TAD gene comprises introduction into a plant of a nucleic acid molecule encoding a TAD protein or a homologue, derivative or active fragment thereof. The nucleic acid may be introduced into a plant by, for example, transformation.

A more preferred way comprises the introduction into a plant of a TAD gene as presented in SEQ ID NO 1. A most preferred way comprises the introduction into a plant of a TAD encoding gene coupled in sense direction to a seed-preferred promoter.

Methods for obtaining enhanced or increased expression of genes or gene products are well documented in the art and include overexpression driven by a suitable promoter and the use of transcription enhancers or translation enhancers. The term overexpression as used herein means any form of expression that is additional to the original wild-type expression level. Preferably the nucleic acid to be introduced into the plant and/or to be overexpressed, is in a sense direction with respect to the promoter to which it is operably linked. The nucleic acid to be overexpressed preferably encodes a TAD protein, further preferably a TAD protein of plant origin. More preferably, the nucleic add molecule encoding the TAD protein is isolated from a dicotyledonous plant, preferably of the family Solanaceae, further preferably the sequence is isolated from *Nicotiana tabacum*. Most preferably the nucleic acid sequence is as represented by SEQ ID NO: 1 or a portion thereof, or encodes an amino acid sequence as represented by SEQ ID NO: 2 or encodes a homologue, derivative or active fragment thereof. However, it should be noted that the applicability of the invention does not rest upon the use of the nucleic acid represented by SEQ ID NO: 1, nor upon the nucleic acid molecule encoding the amino acid sequence of SEQ ID NO: 2, but that other nucleic add molecules encoding homologues, derivatives or active fragments of SEQ ID NO: 2, or portions of SEQ ID NO: 1, or sequences hybridising with SEQ ID NO: 1 may be used in the methods of the present invention.

According to another aspect of the present invention, decreased expression of a nucleic acid sequence is envisaged. Modulating gene expression (whether by a direct or indirect approach) encompasses altered transcript levels of a gene. Altered transcript levels can be sufficient to induce certain phenotypic effects, for example via the mechanism of cosuppression. Here the overall effect of overexpression of a transgene is that there is less activity in the cell of the protein encoded by a native gene having homology to the introduced transgene. Other examples of decreasing expression are also well documented in the art and include, for example, downregulation of expression by anti-sense techniques, co-suppression techniques, RNAi techniques, small interference RNAs (siRNAs), microRNA (miRNA), the use of ribozymes, etc. Therefore according to a particular aspect of the invention, there is provided a method for modulating growth characteristics of plants, including technologies that are based on the synthesis of antisense transcripts, complementary to the mRNA of a TAD gene fragment, or based on RNA interference. Advantageously, the methods according to the present invention may also be practised by downregulation of a nucleic add sequence encoding a TAD. Plants having modified growth characteristics may be obtained by expressing a nucleic acid sequence encoding a TAD in either sense or antisense orientation. Techniques for downregulation are well known in the art. The terms "gene silencing" or "downregulation" of expression, as used herein, refer to lowering levels of gene expression and/or levels of active gene product and/or levels of gene product activity. Such decreases in expression may be accomplished by, for example, the addition of coding sequences or parts thereof in a sense orientation (if it is desired to achieve co-suppression). Therefore, according to one aspect of the present invention, the growth of a plant may be modified by introducing into a plant an additional copy (in full or in part) of a TAD gene fragment already present in a host plant. The additional gene will silence the endogenous gene, giving rise to a phenomenon known as co-suppression.

Genetic constructs aimed at silencing gene expression may comprise the TAD encoding nucleotide sequence, for example as represented by SEQ ID NO: 1 (or one or more portions thereof) in a sense and/or antisense orientation relative to the promoter sequence. The sense or antisense copies of at least part of the endogenous gene in the form of direct or inverted repeats may be utilised in the methods according to the invention. The growth characteristics of plants may also be modified by introducing into a plant at least part of an antisense version of the nucleotide sequence represented, for example, by SEQ ID NO: 1. It should be clear that part of the nucleic acid (a portion) could achieve the desired result. Antisense sequences derived from corresponding genes of the same plant species are preferred to anti-sense sequences derived from homologous genes, whether from the same or other plant species.

Another method for downregulation of gene expression or gene silencing comprises use of ribozymes, for example as described in Atkins et al. 1994 (WO 94/00012), Lenee et al. 1995 (WO 95/03404), Lutziger et al. 2000 (WO 00/00619), Prinsen et al. 1997 (WO 97/3865) and Scott et al. 1997 (WO 97/38116).

Gene silencing may also be achieved by insertion mutagenesis (for example, T-DNA insertion or transposon insertion) or by gene silencing strategies as described by, among others, Angell and Baulcombe 1998 (WO 98/36083), Love et al., 1989 (WO 98/53083), Lederer et al. 1999 (WO 99/15682) or Wang et al. 1999 (WO 99/53050). Expression of an endogenous gene may also be reduced if the endogenous gene contains a mutation. Such a mutant gene may be isolated and introduced into the same or different plant species in order to obtain plants having modified growth characteristics.

Preferably the overexpression of a TAD protein is primarily effected in the seed of a plant, more preferably in the seed endosperm. Alternatively, the overexpression is effected in plant seedlings. Advantageously, performance of the methods according to the present invention results in plants having a variety of modified growth characteristics, such modified growth characteristics including modified yield or biomass, relative to corresponding wild type plants. Preferably, the modified growth characteristics are improved growth characteristics and include increased yield or biomass, relative to corresponding wild type plants.

By "yield" is meant the amount of harvested material per area of production. The term "increased yield" encompasses an increase in biomass in one or more parts of a plant relative to the biomass of corresponding wild-type plants. Depending on the crop, the harvested part of the plant can be a different part or tissue of the plant, such as seed (e.g. rice, sorghum or corn when grown for seed); total above-ground biomass (e.g. corn, when used as silage, sugarcane), root (e.g. sugar beet), fruit (e.g. tomato), cotton fibres, or any other part of the plant which is of economic value. For example, the methods of the present invention are used to increase seed yield of rice and of corn, or also to increase yield of silage corn in terms of overall above ground biomass and energy content. The increase in yield encompasses an increase in seed yield, which includes an increase in the total biomass of the seed (total seed weight) and/or an increase in the number of filled seeds and/or an increase in the total seed number. The increase in yield is also reflected in an increase of the harvest index, which is expressed as a ratio of the yield of harvestable parts, such as seeds, over the total biomass.

Therefore, there is provided a method for increasing yield of a plant, and in particular seed yield, comprising introducing and overexpressing primarily in the seed of this plant a nucleic acid sequence encoding a TAD protein, a homologue, a derivative or an active fragment thereof compared to corresponding wild type plants, and wherein the increase of yield comprises at least one of increased total weight of seeds, increased number of filled seeds, or increased harvest index, each relative to corresponding wild type plants.

Yield is by its nature a complex parameter whereby total yield depends on a number of yield components. The parameters for increased yield of a crop are well known by a person skilled in the art. By way of example, key yield components for corn include number of plants per hectare or acre, number of ears per plant, number of rows (of seeds) per ear, number of kernels is per row, and Thousand Kernel Weight. The improvement in yield as obtained in accordance to the method of the invention, can be obtained as a result in one or more of these yield components. By way of example, key yield components for rice include number of plants per hectare or acre, number of panicles per plant, number of spikelets per panicle, seed filling rate and thousand kernel weight. The improvement in yield as obtained in accordance to the method of the invention can be obtained as a result in one or more of these yield components, preferentially the improvement in yield is obtained primarily on the basis of an increased number of flowers per panicle and an increased seed filling rate.

According to a preferred feature of the present invention, performance of the methods according to the present invention result in plants having modified yield. Preferably, the modified yield is increased seed yield and includes at least an increase in any one or more of number of panicles, number of spikelets per panicle, total seed number, number of filled seeds, total seed weight, Thousand Kernel Weight and harvest index, each relative to control plants. Therefore, according to the present invention, there is provided a method for increasing total weight of seeds, number of filled seeds and/or harvest index of plants, which method comprises modulating expression of a nucleic acid molecule encoding a TAD protein and/or modulating activity of the TAD itself in a plant in a seed preferred way, preferably wherein the TAD protein is encoded by a nucleic acid sequence represented by SEQ ID NO: 1 or a portion thereof or by sequences capable of hybridising therewith or wherein the TAD is represented by SEQ ID NO: 2 or a homologue, derivative or active fragment thereof.

According to a further embodiment of the present invention, genetic constructs and vectors to facilitate introduction and/or expression of the nucleotide sequences useful in the methods according to the invention are provided. Therefore, according to the second embodiment of the present invention, there is provided a gene construct comprising:
  a. a nucleic acid sequence capable of modulating expression of a nucleic acid encoding a TAD protein and/or activity of a TAD protein;
  b. one or more control sequences capable of driving expression of the nucleic acid sequence of (a)
  c. a transcription termination sequence.

Constructs useful in the methods according to the present invention may be created using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein the nucleic acid molecule is operably linked to one or more control sequences allowing expression in prokaryotic and/or eukaryotic host cells.

According to a preferred embodiment of the invention, the genetic construct is an expression vector designed to overexpress the nucleic acid molecule; in particular overexpression primarily obtained in the seed, more particular in the endosperm of the plant seed is aimed at. Additionally and/or alternatively, the expression vector is designed to overexpress the nucleic acid at the seedling stage. The nucleic acid molecule capable of modulating expression of a nucleic acid encoding a TAD protein is preferably a nucleic acid molecule encoding a TAD or a homologue, derivative or active fragment thereof, such as any of the nucleic acid molecules described hereinbefore. A preferred nucleic acid molecule is the sequence represented by SEQ ID NO: 1 or a portion thereof or sequences capable of hybridising therewith or a nucleic acid molecule encoding a sequence represented by SEQ ID NO: 2 or encoding a homologue, derivative or active fragment thereof. Preferably, this nucleic acid is cloned in sense orientation relative to the control sequence to which it is operably linked.

Plants are transformed with a vector comprising the sequence of interest (i.e., the nucleic acid molecule encoding a TAD protein), which sequence is operably linked to one or more control sequences (at least a promoter). The terms "regulatory element", "regulatory sequence", "control sequence" and "promoter" are all used herein interchangeably and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription in initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

In order to obtain desired modified growth characteristics, it is important that the gene of interest is expressed at a suitable level and in a spatially and developmentally suitable pattern. Preferably, the nucleic acid molecule encoding a TAD protein is operably linked to a seed-preferred promoter. The term "seed preferred" promoter as defined herein refers to a promoter that is expressed predominantly in one or more seed tissue(s). Preferably the seed-preferred promoter is an endosperm preferred promoter, more preferably a promoter as presented in GenBank under accession number X65064 (sequence from nucleotide 1 to 672, hereafter named PRO0090), or a promoter of similar strength and/or a similar expression pattern. Therefore, the invention also provides a method for modifying the growth characteristics of a plant, in particular yield, comprising increasing expression in a plant of a nucleic acid encoding a TAD protein, wherein the increased expression is primarily obtained in the seed. Preferably, this expression is effected under control of a seed preferred promoter, more preferably the seed preferred promoter is an endosperm preferred promoter, most preferably the seed preferred promoter is PRO0090. It should be noted however that this PRO0090 promoter is also active in seedlings, hence the methods of the invention can also be practised with the use of a seedling preferred promoter. Therefore, the invention also provides a method for modifying the growth characteristics of a plant, in particular yield, comprising increasing expression in a plant of a nucleic acid encoding a TAD protein, wherein the increased expression is primarily obtained in the seedling.

Promoter strength and/or expression pattern can be analysed for example by coupling the promoter to a reporter gene and assay the expression of the reporter gene in various tissues of the plant. One suitable reporter gene well known to a person skilled in the art is beta-glucuronidase. The promoter strength and/or expression pattern can then be compared to that of a well-characterised reference promoter, such as CaMV 35S promoter or the seed preferred rice prolamin NRP33 promoter. A non limiting list of examples of other seed preferred promoters are presented in Table 1, these promoters or derivatives thereof may also be useful in the methods of the present invention.

TABLE 1

EXEMPLARY SEED-PREFERED PROMOTERS FOR USE IN
THE PERFORMANCE OF THE PRESENT INVENTION

| GENE SOURCE | EXPRESSION PATTERN | REFERENCE |
| --- | --- | --- |
| seed-specific genes | seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| zein | seed | Matzke et al Plant Mol Biol. 14(3): 323-32 1990 |
| napA | seed | Stalberg, et al, Planta 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadins | endosperm | EMBO 3: 1409-15, 1984 |
| barley ltr-1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice α-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| sorgum γ-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |
| putative rice 40S ribosomal protein | weak in endosperm | |
| rice alpha-globulin | strong in endosperm | |
| rice alanine aminotransferase | weak in endosperm | |
| trypsin inhibitor ITR1 (barley) | weak in endosperm | |
| rice WSI18 | embryo + stress | |
| rice RAB21 | embryo + stress | |
| rice oleosin 18kd | aleurone + embryo | |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker proteins include proteins conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

In a preferred embodiment, the genetic construct as mentioned above, comprises a TAD in sense orientation coupled to a promoter that is preferably a seed-preferred and/or seedling preferred promoter, such as for example the PRO0090 promoter. Therefore, another aspect of the present invention is a vector construct comprising an expression cassette essentially similar to SEQ ID NO 3, comprising the PRO0090 promoter, the tobacco TAD gene and the T-zein+T-rubisco transcription terminator sequence. A sequence essentially similar to SEQ ID NO 3 encompasses a first nucleic acid sequence encoding a protein homologous to SEQ ID NO 2 or hybridising to SEQ ID NO 1, which first nucleic acid is operably linked to the PRO0090 promoter, or a promoter with a similar expression pattern and level, and which first nucleic acid is optionally linked to a transcription termination sequence.

The present invention also encompasses plants obtainable by the methods according to the present invention. The present invention therefore provides plants obtainable by the methods according to the present invention, which plants have increased yield, particularly, increased total weight of seeds, increased total seed number, increased number of filled seeds, and/or increased harvest index, and which plants have modulated expression of a nucleic add encoding a TAD protein and/or modulated activity of a TAD protein. Preferably, the modulated expression and/or activity is effected mainly in the seed and/or in the seedling when compared to corresponding wild type plants. Preferably, the modulated expression and/or activity is increased expression and/or activity compared to corresponding wild type plants.

More specifically, the present invention provides a method for the production of transgenic plants having modified growth characteristics, which method comprises:
(i) introducing into a plant or into a plant cell a nucleic acid molecule or a portion thereof encoding a TAD protein or a homologue, derivative or active fragment thereof;
(ii) cultivating the plant cell under conditions promoting regeneration and mature plant growth.

The protein itself and/or the nucleic add itself may be introduced directly into a plant cell or into the plant itself (including introduction into a tissue, organ or any other part of the plant). According to a preferred feature of the present invention, the nucleic acid is preferably introduced into a plant by transformation. The nucleic acid is preferably as represented by SEQ ID NO: 1 or a portion thereof or sequences capable of hybridising therewith, or is a nucleic add encoding an amino acid sequence represented by SEQ ID NO: 2 or a homologue, derivative or active fragment thereof. The nucleic acid sequence is preferably under control of a seed/seedling-preferred promoter, more preferably the PRO0090 promoter.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell can then be used to regenerate a transformed plant in a manner known to persons skilled in the art.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mal. Gen Genet 202, 179-185); DNA or RNA-coated particle bombardment (Klein T. M. et al., 1987, Nature 327, 70) infection with (non-integrative) viruses and the like. A preferred method for rice transformation according to the present invention is the protocol of Hiei et al. (Plant J. 6, 271-282, 1994). Preferred methods to transform corn with a high efficiency are the protocols described in Ishida et al. (1996, Nat Biotechnol. 14, 745-50), and in Frame et al. (2002, Plant Physiol. 129, 13-22), which disclosures are incorporated by reference herein as if fully set forth.

Generally after transformation, plant cells or cell groupings are selected for the presence of one or more markers which are encoded by pant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

In a next step of selection, transformed plants are evaluated for the desired phenotypes. It is well known to persons skilled in the art like plant molecular biologists, that the expression of transgenes in plants, and hence also the phenotypic effect due to expression of such transgene, can differ among different independently obtained transgenic lines and progeny thereof. The transgenes present in different independently obtained transgenic plants differ from each other by the chromosomal insertion locus as well as by the number of transgene copies inserted in that locus and the configuration of those transgene copies in that locus. Differences in expression levels can be ascribed to influence from the chromosomal context of the transgene (the so-called position effect) or from silencing mechanisms triggered by certain transgene configurations (e.g. inwards facing tandem insertions of transgenes are prone to silencing at the transcriptional or post-transcriptional level).

The generated transformed plants may be propagated by a variety of means, such as by clonal propagation or classical breeding techniques. For example, a first generation (or T1) transformed plant may be salted to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention dearly extends to any plant cell or plant produced by any of the methods described herein, and to all plant parts, seeds and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated nucleic acid molecule encoding a TAD protein. Preferred host cells according to the invention are plant cells. The invention also extends to harvestable parts of a plant according to the invention, such as, but not limited to, seeds, leaves, fruits, flowers, stems or stem cultures, rhizomes, roots, tubers and bulbs.

The term "plant" as used herein encompasses whole plants, ancestors and progeny of the plants and plant parts, including seeds, fruits, flowers, shoots, leaves, stems, mots (including tubers), and plant cells, tissues and organs. The term "plant" also therefore encompasses suspension cultures, embryos, meristematic regions, callus tissue, gametophytes, sporophytes, pollen, and microspores. Plants that are particularly useful in the methods of the invention include algae, ferns, and all plants which belong to the superfamily Viridiplantae, in particular monocotyledonous and dicotyledonous plants, including fodder or forage legumes, ornamental plants, food crops, trees, or shrubs selected from the list comprising *Abelmoschus* spp., *Acer* spp., *Actinidia* spp., *Agropyron* spp., *Allium* spp., *Amaranthus* spp., *Ananas comosus*, *Annona* spp., *Apium graveolens*, *Arabidopsis thaliana*, *Arachis* spp, *Artocarpus* spp., *Asparagus officinalis*, *Avena sativa*, *Averrhoa carambola*, *Benincasa hispida*, *Bertholletia excelsea*, *Beta vulgaris*, *Brassica* spp., *Cadaba farinosa*, *Camellia sinensis*, *Canna indica*, *Capsicum* spp., *Carica papaya*, *Carissa macrocarpa*, *Carthamus tinctorius*, *Carya* spp., *Castanea* spp., *Cichorium endivia*, *Cinnamomum* spp., *Citrullus lanatus*, *Citrus* spp., *Cocos* spp., *Coffea* spp., *Cola* spp., *Colocasia esculenta*, *Corylus* spp., *Crataegus* spp., *Cucumis* spp., *Cucurbita* spp., *Cynara* spp., *Daucus carota*, *Desmodium* spp., *Dimocarpus longan*, *Dioscorea* spp., *Diospyros* spp., *Echinochloa* spp., *Eleusine coracana*, *Eriobotrya japonica*, *Eugenia uniflora*, *Fagopyrum* spp., *Fagus* spp., *Ficus carica*, *Fortunella* spp., *Fragaria* spp., *Ginkgo biloba*, *Glycine* spp., *Gossypium hirsutum*, *Helianthus* spp., *Hibiscus* spp., *Hordeum* spp., *Ipomoea batatas*, *Juglans* spp., *Lactuca sativa*, *Lathyrus* spp., *Lemna* spp., *Lens culinaris*, *Linum usitatissimum*, *Litchi chinensis*, *Lotus* spp., *Luffa acutangula*, *Lupinus* spp., *Macrotyloma* spp., *Malpighia emarginata*, *Malus* spp., *Mammea americana*, *Mangifera indica*, *Manihot* spp., *Manilkara zapota*, *Medicago saliva*, *Melilotus* spp., *Mentha* spp., *Momordica* spp., *Morus nigra*, *Musa* spp., *Nicotiana* spp., *Olea* spp., *Opuntia* spp., *Ornithopus* spp., *Oryza* spp., *Panicum miliaceum*, *Passiflora edulis*, *Pastinaca sativa*, *Persea* spp., *Petroselinum crispum*, *Phaseolus* spp., *Phoenix* spp., *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Rubus* spp., *Saccharum* spp., *Sambucus* spp., *Secale cereale*, *Sesamum* spp., *Solanum* spp., *Sorghum bicolor*, *Spinacia* spp., *Syzygium* spp., *Tamarindus indica*, *Theobroma cacao*, *Trifolium* spp., *Triticosecale rimpaui*, *Triticum* spp., *Vaccinium* spp., *Vicia* spp., *Vigna* spp., *Vitis* spp., *Zea mays*, *Zizania palustris*, *Ziziphus* spp., amongst others.

The methods of the present invention are favourable to apply to crop plants because the methods of the present invention are used to increase yield, in particular the seed yield, more particular total weight of seeds, number of filled seeds and harvest index of a plant. Therefore, the methods of the present invention are particularly useful for crop plants cultivated for their seeds, such as cereals, sunflower, soybean, cotton, pea, flax, lupines, canola etc, but are also useful for crops that are cultivated for their biomass. According to a preferred feature of the present invention, the plant is a crop plant comprising soybean, sunflower, canola, alfalfa, rapeseed or cotton. Further preferably, the plant according to the present invention is a monocotyledonous plant, including members of the Poaceae, such as sugarcane, most preferably a cereal, such as rice, maize, wheat, millet barley and sorghum. Accordingly, a particular embodiment of the present invention relates to a method to increase yield, in particular total weight of seeds, number of filled seeds, total seed number and/or harvest index of a cereal.

The present invention also relates to the use of an isolated nucleic acid encoding a TAD protein and to the use of portions thereof or nucleic acids hybridising therewith in modifying the growth characteristics of plants, preferably in increasing the yield of a plant, more preferably seed yield, in particular the total weight of seeds, the number of filled seeds, total seed number and/or the harvest index of a plant, and wherein the nucleic acid encoding a TAD protein, the portions thereof or the nucleic acids hybridising therewith are expressed in a seed preferred manner. The present invention also relates to use of a TAD protein and to the use of homologues, derivatives and active fragments thereof. In modifying the yield of plants, in particular the use for increasing the total weight of seeds, the number of filled seeds, total seed number and/or the harvest index of plants. The nucleic acid sequence is preferably as represented by SEQ ID NO: 1 or a portion thereof or sequences capable of hybridising therewith or encodes an amino acid sequence represented by SEQ ID NO: 2 or a homologue, derivative or active fragment thereof. The invention encompasses also the use of plants or plant parts (including seeds) for processing, which plants or plant parts have modulated expression of a nucleic acid encoding a TAD protein and/or modulated activity of a TAD protein. Such uses for processing include for example the use in food or feed production, in brewing, in the production of industrial proteins or pharmaceuticals, in sugar or oil production.

The methods according to the present invention result in plants having modified growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features. Accordingly, the methods of the present invention can also be used in so-called "gene stacking" procedures.

The present invention will now be described with reference to the following figures in which:

FIG. 2: Binary vector for the expression in Oryza sativa of the Nicotiana tabacum BY2 cells TOB3-like AAA-ATPase domain gene (CDS0671) under the control of the endosperm/seedling preferred promoter PRO0090. This vector contains a T-DNA derived from the Ti Plasmid, limited by a left border (LB repeat, LB Ti C58) and a right border (RB repeat, RB Ti C58)). From the left border to the right border, this T-DNA contains: a plant selectable marker and a screenable marker for selection and screening of transformed plants; the PRO0090-CDS0671-zein and rbcS-deltaGA double terminator cassette for expression of the Nicotiana tabacum BY2 cells TOB3-like AAA-ATPase domain gene. This vector also contains an origin of replication from pBR322 for bacterial replication and a selectable marker (Spe/SmeR) for bacterial selection with spectinomycin and streptomycin.

EXAMPLES

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1984), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Cloning of CDS0671

Cloning of the TAD Gene Fragment from Tobacco

A cDNA-AFLP experiment was performed on a synchronized tobacco BY2 cell culture (Nicotiana tabacum L. cv. Bright Yellow-2), and BY2 expressed sequence tags that were cell cycle modulated were elected for further cloning. The expressed sequence tags were used to screen a tobacco cDNA library and to isolate the cDNA of interest, namely one coding for TOB3-like AAA-ATPase domain gene (CDS0671).

Synchronization of BY2 Cells.

A tobacco BY2 (Nicotiana tabacum L. cv. Bright Yellow-2) cultured cell suspension was synchronized by blocking cells in early S-phase with aphidicolin as follows. The cell suspension of Nicotiana tabacum L. cv. Bright Yellow 2 was maintained as described (Negate et al. Int. Rev. Cytol. 132, 1-30, 1992). For synchronization, a 7-day-old stationary culture was diluted 10-fold in fresh medium supplemented with aphidicolin (Sigma-Aldrich, St Louis, Mo.; 5 mg/l), a DNA-polymerase α inhibiting drug. After 24 h, cells were released from the block by several washings with fresh medium after whichtheir cell cycle progression resumed.

RNA Extraction and cDNA Synthesis.

Total RNA was prepared using LiCl precipitation (Sambrook et al, 2001) and poly(A$^+$) RNA was extracted from 500 µg of total RNA using Oligotex columns (Qiagen, Hiden, Germany) according to the manufacturer's Instructions. Starting from 1 µg of poly(A$^+$) RNA, first-strand cDNA was synthesized by reverse transcription with a biotinylated oligo-dT25 primer (Genset, Paris, France) and Superscript II (Life Technologies, Gaithersburg, Md.). Second-stand synthesis was done by strand displacement with Escherichia coli ligase (Life Technologies), DNA polymerase I (USB, Cleveland, Ohio) and RNAse-H (USB).

CDNA-AFLP Analysis.

Five hundred ng double-stranded cDNA was used for AFLP analysis as described (Vos et al., Nucleic Acids Res. 23 (21) 4407-4414, 1995; Bachem et al., Plant J. 9 (5) 745-53, 1996) with modifications. The restriction enzymes used were BstYI and MseI (Biolabs) and the digestion was done in two separate steps. After the first restriction digest with one of the enzymes, the 3' end fragments mere trapped on Dyna beads (Dynal, Oslo, Norway) by means of their biotinylated tail, while the other fragments were washed away. After digestion with the second enzyme, the released restriction fragments were collected and used as templates in the subsequent AFLP steps. For pre-amplifications, a MseI primer without selective nucleotides was combined with a BstYI primer containing either a T or a C as 3' most nucleotide. PCR conditions were as described (Vos et al., 1995). The obtained amplification mixtures were diluted 600-fold and 5 µl was used for selective amplifications using a P33-labeled BstYI primer and the Amplitaq-Gold polymerase (Roche Diagnostics, Brussels, Belgium). Amplification products were separated on 5% polyacrylamide gels using the Sequigel system (Biorad). Dried gels were exposed to Kodak Biomax films as well as scanned in a Phosphorimager (Amersham Pharmacia Biotech, Little Chalfont, UK).

Characterization of AFLP Fragment.

Bands corresponding to differentially expressed transcripts, among which the (partial) transcript corresponding to SEQ ID NO 1 (or CDS0671), were isolated from the gel and eluted. DNA was reamplified under the same conditions as for selective amplification. Sequence Information was obtained either by direct sequencing of the reamplified polymerase chain reaction product with the selective BstYI primer or after cloning the fragments in pGEM-T easy (Promega, Madison, Wis.) and sequencing of individual cones. The obtained sequences were compared against nucleotide and protein sequences present in the publicly available databases by BLAST sequence alignments (Altschul at al., Nucleic Acids Res. 25 (17) 3389-3402 1997). When available, tag sequences were replaced with longer EST or isolated cDNA sequences to increase the chance of finding significant homology. The physical cDNA done corresponding to SEQ ID NO 1 (CDS0671) was subsequently amplified from a commercial Tobacco cDNA library as follows.

Cloning of the TAD Gene Fragment (COS0671)

A cDNA library with an average size of inserts of 1,400 bp was prepared from poly(A$^+$) RNA isolated from actively dividing, non-synchronized BY2 tobacco cells. These library-inserts were cloned in the vector pCMVSPORT6.0, comprising an attB GATEWAY cassette (an attB recombinant cassette—Life Technologies). From this library, 46,000 clones were selected, arrayed in 384-well microtiter plates, and subsequently spotted in duplicate on nylon filters. The arrayed clones were screened using pools of several hundreds of radioactively labelled tags as probe (including the BY2-tag corresponding to the sequence CDS0671, SEQ ID NO 1). Positive clones were isolated (among which was the done corresponding to CDS0671, SEQ ID NO 1), sequenced, and aligned with the tag sequence. In cases where hybridisation with the tag failed, the full-length cDNA corresponding to the tag was selected by PCR amplification: tag-specific primers were designed using primer3 program (URL genome.wi.m-it.edu/genome software/other/primer3) and used in combination with a common vector primer to amplify partial cDNA inserts. Pools of DNA from 50,000, 100,000, 150,000, and 300,000 cDNA clones were used as templates in the PCR amplifications. Amplification products were then isolated from agarose gels, cloned, sequenced and their sequence aligned with those of the tags.

Figure 1:
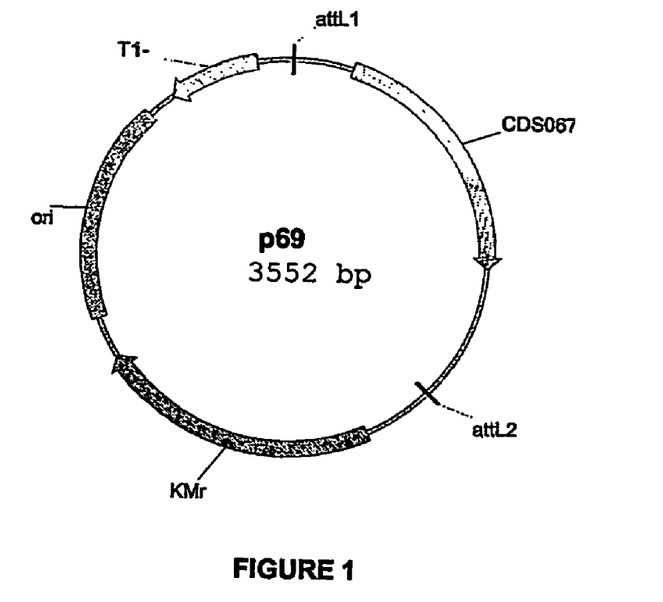
FIG. 1: Schematic presentation of the entry clone p69, containing CDS0671 within the AttL1 and AttL2 sites for GATEWAY-cloning (bacteriophage lambda site specific recombinant cloning) in the pDONR201 backbone. CDS0671 is the internal code for the TOB3-like AAA-ATPase domain coding sequence of Nicotiana tabacum BY2 cells. This vector contains also a bacterial kanamycine-resistance cassette and a bacterial origin of replication.

Next, the full-length cDNA corresponding to the nucleotide sequence of SEQ ID NO 1 was cloned from the pCM-Vsport6.0 library vector into pDONR201, a GATEWAY donor vector (a donor vector—Invitrogen, Paisley, UK) via a LR reaction, resulting in the entry done p69 (FIG. 1).

Example 2

Vector Construction for Transformation with PRO0090-CDS0671 Cassette

The entry clone p69 was subsequently used in an LR reaction with p0830, a destination vector used for *Oryza sativa* transformation. This vector contains as functional elements within the T-DNA borders: a plant selectable marker; a screenable marker; and a GATEWAY cassette (recombinant cassette) intended for LR in vivo recombination with the sequence of interest already cloned in the entry clone. Promoter PRO0090 was located upstream of this GATEWAY cassette.

Figure 2:
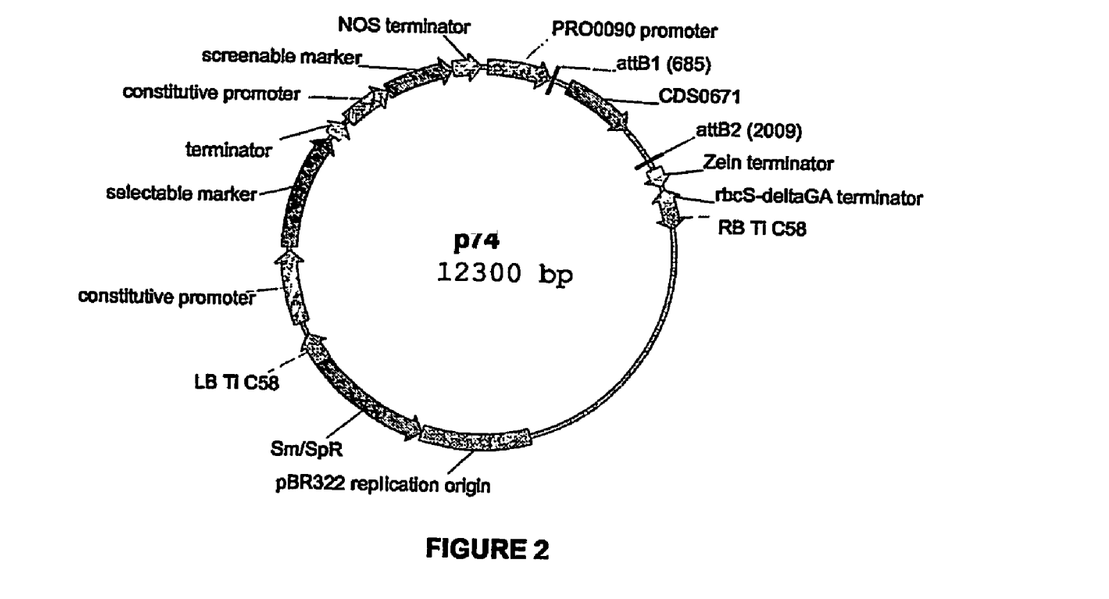
Figure 3:
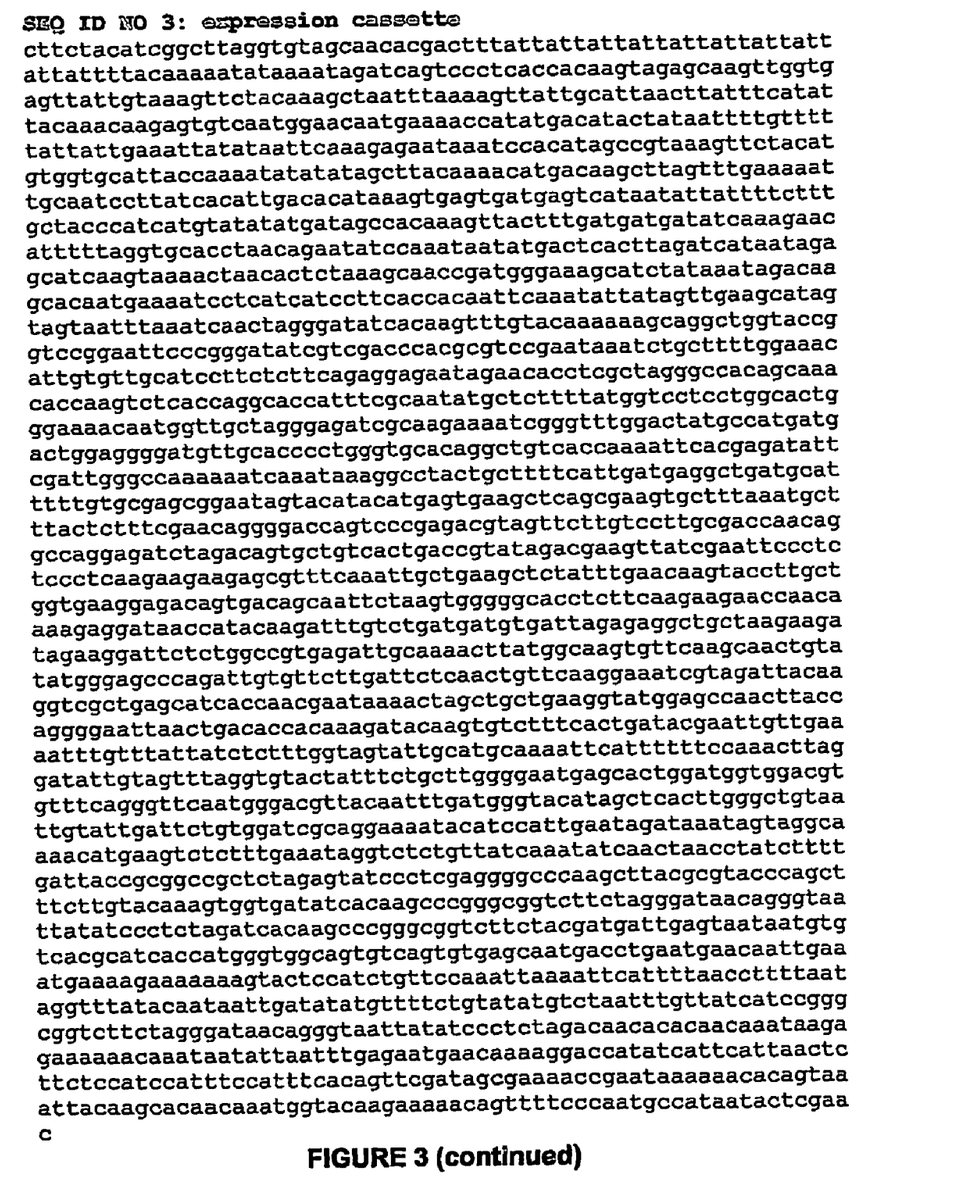
FIG. 3: Sequence listing.

After the LR recombination step, the resulting expression vector p74 (FIG. 2) was transformed into *Agrobacterium* strain LBA4044 and subsequently into *Oryza sativa* plants.

Example 3

Transformation of Rice with PRO0129 up-CDS0716

Mature dry seeds of *Oryza sativa* japonica cultivar Nipponbare were dehusked. Sterilization was done by incubating the seeds for one minute in 70% ethanol, followed by 30 minutes in 0.2% $HgCl_2$ and by 6 washes of 15 minutes with sterile distilled water. The sterile seeds were then germinated on a medium containing 2,4-D (callus induction medium). After a 4-week incubation in the dark, embryogenic, scutellum-derived calli were excised and propagated on the same medium. Two weeks later, the calli were multiplied or propagated by subculture on the same medium for another 2 weeks. 3 days before co-cultivation, embryogenic callus pieces were sub-cultured on fresh medium to boost cell division activity. The *Agrobacterium* strain LBA4404 harbouring the binary vector p3076 was used for co-cultivation. The *Agrobacterium* strain was cultured for 3 days at 28° C. on AB medium with the appropriate antibiotics. The bacteria were then collected and suspended in liquid co-cultivation medium at an $OD_{600}$ of about 1. The suspension was transferred to a petri dish and the calli were immersed in the suspension during 15 minutes. The callus tissues were then blotted dry on a filter paper, transferred to solidified co-cultivation medium and incubated for 3 days in the dark at 25° C.

Co-cultivated callus was then grown on 2,4-D-containing medium for 4 weeks in the dark at 28° C. in the presence of a selective agent at a suitable concentration. During this period, rapidly growing resistant callus islands developed. Upon transfer of this material to a regeneration medium and incubation in the light, the embryogenic potential was released and shoots developed in the next four to five weeks. Shoots were excised from the callus and incubated for 2 to 3 weeks on an auxin-containing medium from which they were transferred to soil. Hardened shoots were grown under high humidity and short days in a greenhouse. Finally seeds were harvested three to five months after transplanting. The method yielded single locus transformants at a rate of over 50% (Aldemita and Hodges, 1996, Chan et al., 1993, Hiei et al., 1994).

Example 4

Evaluation of Transgenic Rice Transformed with PRO0129-CDS1585

Approximately 15 to 20 independent T0 rice transformants were generated. The primary transformants were transferred from tissue culture chambers to a greenhouse for growing and harvest of T1 seed. 7 events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring screenable marker expression.

The selected T1 plants were transferred to a greenhouse. Each plant received a unique barcode label to unambiguously link the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity each plant was passed several times through a digital imaging cabinet. At each time point, digital images (2048×1536 pixels, 16 million colours) were taken of each plant from at least 6 different angles.

The mature primary panicles were harvested, bagged, barcode-labelled and then dried for three days in an oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the following set of seed-related parameters:
  (i) Number of filled seeds: was determined by counting the number of filled husks that remained after the separation step.
  (ii) Total seed weight per plant the yield was measured by weighing all filled husks harvested from a plant.
  (iii) Harvest index of plants: the harvest index in the present invention is defined as the ratio between the total seed weight and the above ground area ($mm^2$), multiplied by a factor $10^8$.

These parameters were derived in an automated way from the digital images using image analysis software and were analysed statistically. A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein a "global gene effect". A significant value for the F test shows there is a "gene" effect, meaning that it is not only the presence or the position of the gene that is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "Null segregants" or "Nullizygotes" are the plants treated in the same way as the transgenic plant, but from which the transgene has segregated. Null plants can also be described as the homozygous negative transformed plants. The threshold for significance for the t-test is set at a 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Vegetative growth and seed yield were measured according to the methods as described above. It was found that the total weight of seeds, the number of filed seeds and the harvest index were increased in the plants transformed with the TAD coding sequence when compared the control plants without the TAD coding sequence.

The data obtained in the first experiment were confirmed in a second experiment with T2 plants. Seed batches from the positive plants (both hetero- and homozygotes) in T1, were screened by monitoring marker expression. For each chosen event the heterozygote seed batches were then retained for T2 evaluation. Within each seed batch an equal number of positive and negative plants were grown in the greenhouse for evaluation. Three lines that had the correct expression pattern were selected for further analysis.

A total number of 120 TAD transformed plants were evaluated in the T2 generation, that is 40 plants per event of which 20 were positive for the transgene and 20 negative.

Example 5

Results of the Evaluation of Transgenic Plants Transformed with PRO0090-CDS0671

In generation T1, 4 of the 5 tested lines showed an increase in the number of filled seeds, the total weight of seeds and in the harvest index. For the best line (line 21), such increase amounted to around 50% for three different seed yield parameters, each with a low p-value (Table 2).

TABLE 2 increase of seed yield for line 21

| Parameter | % increase | p-value |
| --- | --- | --- |
| Total seed weight | 58 | 0.0611 |
| Number of filled seeds | 58 | 0.0403 |
| Harvest Index | 47 | 0.0210 |

The mean increase calculated from the data of the four positive T1 lines and the three T2 lines that were taken for confirmation, versus the nullizygous plants for the different seed yield parameters is listed in Table 3.

TABLE 3 mean increase in seed yield in T1 and T2 generation

| parameter | T1, % increase | T2, % increase | p-value, T1 and T2 combined |
| --- | --- | --- | --- |
| Total seed weight | 34 | 34 | 0.0058 |
| Number of filled seeds | 37 | 27 | 0.0134 |
| Harvest Index | 25 | 24 | 0.0053 |

The results for the T1 plants were confirmed with T2 plants. Here too, there was an increase for the various parameters (Table 3). When the data for the T1 and T2 plants were combined and re-analysed, the positive effects for the number of filed seeds, the total weight of seeds and the harvest index were found to be highly significant (see p-values in Table 3, right hand column).

Example 6

Use of the Invention in Corn

The invention described herein can also be used in maize. To this aim, the TAD gene, or the maize orthologue thereof is cloned under control of a suitable promoter, preferably a seed and/or seedling preferred promoter in a plant transformation vector suited for *Agrobacterium*-mediated corn transformation. Such vectors and methods for corn transformation have been described in literature (EP0604662, EP0672752, EP0971578, EP0955371, EP0558676, Ishida et al. 1996; Frame et al., 2002). Transgenic plants made by these methods are grown in the greenhouse for T1 seed production. Heritability is checked by progeny segregation analysis. Copy number of the transgene is checked by quantitative real-time PCR and/or Southern blot analysis. Expression levels of the transgene are determined by reverse PCR and/or Northern analysis. Transgenic lines with single copy insertions of the transgene and with varying levels of transgene expression are selected for T2 seed production through selfing or for crossing to different germplasm. Progeny seeds are germinated and grown in the field or in the greenhouse in conditions well adapted for make (16:8 hr photoperiod, 26-28° C. daytime and 22-24° C. night time temperature) as well under water-deficient, nitrogen-deficient, and excess NaCl conditions. In the case of selfing, null segregants from the same parental line, as well as wild type plants of the same cultivar are used as controls. In the case of crossing, transgenics, null segregants and wild type plants of the same cultivar are crossed to a chosen parent and F1 plants from the transgenic cross are compared to F1 plants from the null segregant and the wild type crosses. The progeny plants resulting from the selfing or the crosses are evaluated on different biomass and growth parameters, including plant height, stem thickness, number of leaves, total above ground area, leaf greenness, time to maturity, flowering time, ear number, harvesting time. The seeds of these lines are also checked on various parameters, such as grain size, total grain yield per plant, and grain quality (starch content, protein content and oil content). Lines that are most significantly improved versus the controls for any of the above-mentioned parameters are selected for further field testing and marker-assisted breeding, with the objective of transferring the field-validated transgenic traits into commercial germplasm. Methods for testing maize for growth and yield-related parameters in the field are well established in the art, as are techniques for introgressing specific loci (such as transgene containing loci) from one germplasm into another.

The invention claimed is:

1. Method for increasing seed yield of a plant compared to corresponding control plants by introducing an expression cassette comprising a nucleic acid sequence encoding a polypeptide of SEQ ID NO:2, wherein said plant has increased seed yield.

2. Method of claim 1, wherein said increased seed yield comprises at least an increase in the number of filled seeds.

3. Method of claim 1, wherein said increased seed yield comprises at least an increase in total seed weight.

4. Method of claim 1, wherein said increased seed yield comprises at least an increase in Harvest Index.

5. Method for the production of a transgenic plant having increased seed yield compared to corresponding control plants, which method comprises:
   a) introducing into a plant or plant cell a nucleic acid sequence encoding a polypeptide of SEQ ID NO:2;
   b) cultivating the plant or plant cell under conditions promoting regeneration and mature plant growth.

* * * * *